United States Patent [19]

Bateman et al.

[11] Patent Number: 4,990,335

[45] Date of Patent: Feb. 5, 1991

[54] USE OF VINYL ALCOHOL HOMOPOLYMER AND COPOLYMERS FOR TABLETING ACTIVE MATERIALS

[75] Inventors: Linda R. Bateman; Robert C. Di Luccio; Clare A. Stewart, Jr., all of Wilmington, Del.; Donna L. Visioli, Lower Swynedd, Pa.; David P. Beach-Coffin, Lindenhurst, N.Y.

[73] Assignee: E. I. du Pont de Nemours and Company, Wilmington, Del.

[21] Appl. No.: 165,230

[22] Filed: May 12, 1988

Related U.S. Application Data

[63] Continuation-in-part of Ser. No. 29,996, Mar. 25, 1987.

[51] Int. Cl.$^5$ .............................................. A01N 25/34
[52] U.S. Cl. ................................. 424/408; 424/409; 424/410; 424/468; 424/469; 424/470
[58] Field of Search ............... 424/464, 468, 469, 470, 424/501, 486, 409, 408, 410

[56] References Cited

U.S. PATENT DOCUMENTS

| | | | |
|---|---|---|---|
| 3,108,046 | 10/1963 | Harbit | 424/470 |
| 4,415,547 | 11/1983 | Yu et al. | 424/469 |
| 4,499,066 | 2/1985 | Moro et al. | 424/465 |
| 4,800,087 | 1/1989 | Mehta | 424/494 |
| 4,837,032 | 6/1989 | Ortega | 424/486 X |

Primary Examiner—Thurman K. Page

[57] ABSTRACT

Method of making tablets for active ingredient delivery by compressing a mixture of active ingredient and granular, high viscosity, fully hydrolyzed polyvinyl alcohol or copolymer of vinyl alcohol with methyl acrylate or methyl methacrylate. By use of a crystalline, heat treated polymer, a tablet providing quick active ingredient release is obtained. By using an amorphous, non-heat treated polymer a tablet providing prolonged active ingredient release is obtained. By using blends of crystalline and amorphous polymers, tablets having a range of active ingredient release characteristics can be obtained. The granular, high viscosity, fully hydrolyzed polymers provide flowability, compressibility and processing versatility advantages over conventional tablet binders.

21 Claims, 5 Drawing Sheets

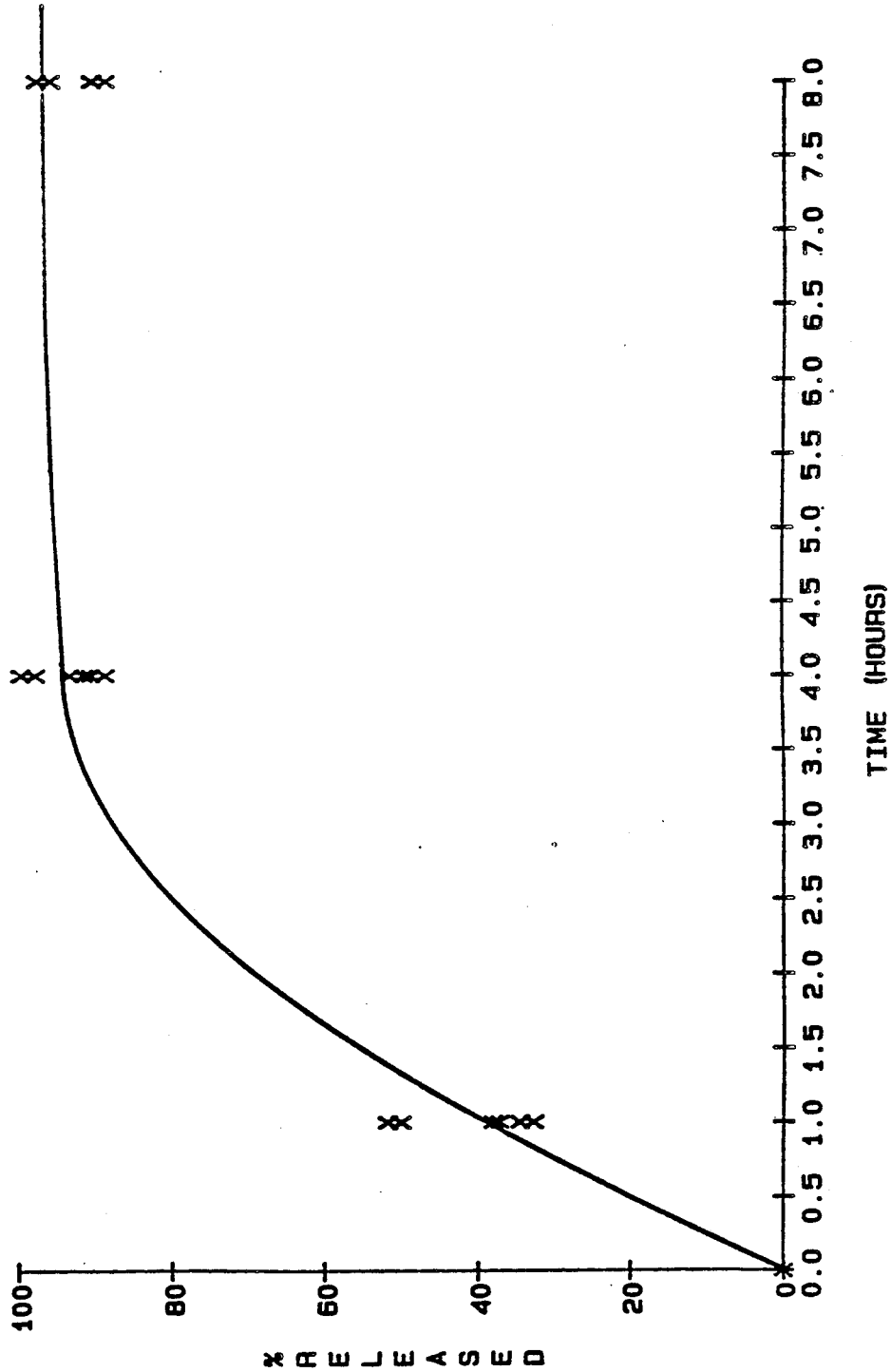

USE OF VINYL ALCOHOL HOMOPOLYMER AND COPOLYMERS FOR TABLETING ACTIVE MATERIALS

CROSS-REFERENCE TO RELATED APPLICATION

This is a continuation in part of our application Ser. No. 29,996 filed on behalf of four of the present inventors Mar. 25, 1987.

FIELD OF THE INVENTION

This invention relates to the manufacture of compressed tablets for such uses as oral drug delivery for medical or veterinary use, delivery of pesticides and herbicides to the application sites, and dispensing measured quantities of personal care products, more particularly the manufacture of tablets having a range of the active ingredient release characteristics from instant to prolonged, utilizing homopolymer and copolymers of vinyl alcohol as binder.

BACKGROUND OF THE INVENTION

Compressed tablets for such uses as oral drug delivery are prepared by three methods—wet granulation, dry granulation and direct compression. Each method involves mixing powdered drug substance with a powdered binder material and compressing the mixture in a tableting machine. In the wet granulation method the mixture is granulated before compression by wetting with a solution of the binder while stirring, wet screening, drying and dry screening. In the dry granulation method the mixture is granulated before compression by dry-compacting then dry screening. In the direct compression method the powder mixture is compressed to form the tablet without intermediate granulation.

Binders which are used commercially in the manufacture of compressed tablets include lactose, hydroxypropylmethylcellulose, microcrystalline cellulose, acacia mucilage, tragacanth mucilage, starch mucilage, alginates, sugar and polyvinyl-pyrrolidone. Commercial prolonged-action tablets include tablets with slow-release cores, tableted mixed-release granules, multiple-layer tablets, drug-filled porous inert plastic pellets, and tablets of drug-ion exchange resin complexes. These are relatively complex formulations compared to conventional quick-release tablets and are thus more costly to manufacture. U.S. Pat. Nos. 3,870,790, 4,226,849 and 4,389,393 disclose sustained-release tablets made by conventional tablet-making methods using certain hydroxypropylmethylcelluloses (HPMC's) as binders. Although the HPMC's are being used commercially, their bulk flow characteristics and compressibility are rather poor; typically granulation prior to compression and high compression pressures are required, which may affect process and product reproducibility and add to the cost of manufacture.

Suess, Pharmazie, 38, No. 7, 476-8 (1983) describes preparation of compressed tablets by the direct compression method using polyvinyl alcohol (PVA) and drug substance. Inclusion of various quantities of magnesium stearate to provide delayed release is described. Protracted release was correlated to addition of other excipients, i.e., potato starch and magnesium stearate, rather than inclusion of PVA. Physical and chemical characteristics of the PVA used are not described. However, most commercially available PVA, because of its method of manufacture, is only partially hydrolyzed and consists of non-spheroidal particles with size distribution such that more than 50% of the material is retained on a 60 mesh (0.246 mm opening) Tyler screen. Such PVA particles have erratic flow and compressibility characteristics.

PVA has also been used to prepare controlled release drug formulations other than compressed tablets. For example, Korsmeyer et al., Journal of Membrane Science, 9, 211-227 (1981) describes preparation of PVA gels containing drug substance for controlled drug release. The gels were made by swelling PVA in water, adding drug substance and cross-linking with glutaraldehyde. The PVA used by Korsmeyer et al. was Elvanol® grade 85-82 from E. I. du Pont de Nemours and Company, Wilmington, Del. Korsmeyer et al. describes this PVA as an amorphous and a tactic polymer with number average molecular weight $\overline{M}n=52,800$, poly-dispersity index $\overline{M}w/\overline{M}n=2.14$, and degree of hydrolysis=99.8%. Keith et al. U.S. Pat. No. 4,291,014 discloses dissolving PVA and polyvinylpyrrolidone in water, adding a drug substance and pouring the mixture into forms to provide a diffusion matrix for controlled drug release. Numerous patents and published applications disclose controlled release oral formulations comprising drug substance in powder, pill, tablet or capsule form having a polymer coating comprising PVA. Examples of such patents and applications are PCT publication Nos. WO 85/03436, WO 85/03437, EPO publication Nos. 0 063 014; 0 076 428; U.S. Pat. Nos. 4,205,060, 4,432,965; and U.K. publication No. GB 2042892A. German published application No. 30 42 916 discloses a tablet made by applying a drug to the surface of a film of polyvinyl alcohol or a fiber fleece bonded with polyvinyl alcohol.

Compressed tablets containing other active ingredients such as, for example, pesticides or herbicides; fertilizers, especially for use on house plants; personal care products such as, for example, denture cleaners; household preparations such as, for example, bathroom cleaners, have been used to a lesser degree, either because of the high cost of tableting those materials relative to their value in use or because of the difficulty in controlling the rate of release of the active ingredient to the desired extent.

Tableting agricultural formulations such as, e.g., pesticides or herbicides offers many advantages over the usual dusts, powders, and granules. For example, tableting does not adversely affect heat-labile materials since it requires no heat; it prevents or reduces health and environment hazards encountered in the case of dusts and powders (and even granules); and it permits release of the active ingredient at a controlled rate.

Herbicides often are added in fertilizer solutions. Currently, they are supplied as dry flowable powders, which must be measured by the farm operator before adding to the fertilizer spray tank. This causes waste and exposes the operator to a biologically active material. Herbicides used for crop dusting need to have increased density and very specific geometry for accurate application.

Slugs are a serious pest to crops in many parts of the world. Current slug baits, consisting of wheat flour, pesticide, and paraffin wax binder, break up rapidly on exposure to damp earth and rain. A longer release slug bait would be very desirable.

Tableting solves all the above problems of the current agricultural formulations.

Industrial chemicals such as, e.g., oxidizing agents used for the purification and sanitation of spas and swimming pools normally are rapidly released into water shortly after their application. It would be desirable to control the rate of their release in order to minimize the frequency of their application and to avoid wide fluctuations in concentration.

Personal care products such as, e.g., denture cleaners and contact lens cleaners in tablet form permit the user to employ a predetermined effective amount of the active ingredient.

Veterinary chemicals in tablet form permit controlled release of nutritional supplements for animals such as dairy and beef cattle.

SUMMARY OF THE INVENTION

We have found that pharmaceutically elegant and esthetically appealing compressed tablets having a range of active ingredient release characteristics, from substantially instant to prolonged release, can be made by the wet granulation, dry granulation or direct compression method, using a mixture of active ingredient and binder consisting essentially of at least one polymer selected from the group consisting of polyvinyl alcohol and copolymers of vinyl alcohol with up to about 10 mole percent methyl acrylate or methyl methacrylate, provided the polymer has certain required chemical and physical characteristics, described below.

By pharmaceutically elegant and esthetically appealing tablets we mean tablets which have suitable hardness and coherence, excellent appearance and excellent uniformity of weight, physical dimensions and hardness. The vinyl alcohol polymers permit formulation of tablets which have active ingredient release characteristics which are independent of processing changes and which are predictable (in vitro) using classical diffusion controlled modeling techniques. They also permit formulation of tablets which have the desirable characteristic of floating in water, and continuing to float when thoroughly wetted.

The physical and chemical characteristics which the vinyl alcohol homopolymer or copolymer must possess for use in this invention are the following: number average molecular weight $\overline{M}n$ in the range of about 25,000 to 100,000; polydispersity ($\overline{M}w/\overline{M}n$) in the range of about 1.4 to 2.6, where $\overline{M}w$ is weight average molecular weight; viscosity in the range of about 10 to 70 mPa.sec; area in the range of about 0.6 to 6.0 $m^2/g$; percent hydrolysis of at least 98%; and in the form of spheroidal particles arranged in spheroidal clusters, with a size distribution such that less than about 5% of the polymer is retained on a 20 mesh (0.833 mm) screen; less than about 50% is retained on an 80 mesh (0.175 mm) screen; and more than about 70% is retained on a 200 mesh (0.074 mm) screen. Preferably, more than about 90% is retained on a 400 mesh (0.038 mm) screen. Vinyl alcohol polymers having particles of the described shape and size are referred to herein as granular polymers.

Throughout this specification and the claims, parts and percentages are by weight, unless otherwise specified. Vinyl alcohol polymers are made by hydrolysis or alcoholysis of vinyl acetate polymers. Percent hydrolysis refers to the mole percent hydrolysis or alcoholysis of acetate groups, dry basis. Also, throughout this specification and the claims, viscosity figures are in mPa.sec for 4% aqueous solutions measured by the Hoeppler falling ball method; surface areas are in $m^2/g$ measured by the BET method; and sieve sizes refer to the Tyler sieve series.

Granular vinyl alcohol polymers having the characteristics described exhibit excellent flow and compression characteristics, and therefore provide significant processing and cost advantages in the manufacture of compressed tablets. In a standard flowability test using a Hanson Flowdex ®, we have found that a polymer useful in this invention is capable of flowing spontaneously through an orifice of 10 millimeter diameter. Using a standard Strong-Cobb instrument for testing tablet hardness, we have found that the vinyl alcohol polymers described, when compressed without other ingredients, using a compression pressure of $12.3 \times 10^6$ kg/m$^2$, provide tablets having a hardness of at least 30 Strong-Cobb units (SCU). Microcrystalline cellulose and hydroxypropylmethylcellulose used commercially as tablet binder and non-granular vinyl alcohol polymers do not exhibit the desirable flowability and compressibility characteristics of the granular vinyl alcohol polymers used in this invention. Although wet granulation can be used in the method of this invention, dry granulation or direct compression is satisfactory. Direct compression is usually adequate and is preferred.

We have found that vinyl alcohol polymers which are at least partially crystalline, as a result of being heat-treated after alcoholysis, provide tablets which give substantially immediate active ingredient release, e.g., substantially 100% of the active ingredient is released within 30 minutes or less. Such tablets are novel, and constitute an embodiment of this invention.

Vinyl alcohol polymers which are not heat-treated and are substantially amorphous provide tablets which give prolonged active ingredient release, e.g., 24 hours or longer to release the active ingredient. By blending crystalline and amorphous polymers in various ratios, tablets having a range of active ingredient release characteristics can be provided.

Tablets in which a substantial portion of the binder, e.g., about 30%–100% by weight, is a copolymer of vinyl alcohol with 1 to 10 mole percent methyl acrylate or methyl methacrylate, are also novel and constitute an embodiment of this invention.

DESCRIPTION OF THE DRAWINGS

FIG. 5 is a plot showing dissolution profile of potassium monopersulfate from PVA tablets prepared according to Example 6.

DETAILED DESCRIPTION

Figure 1:
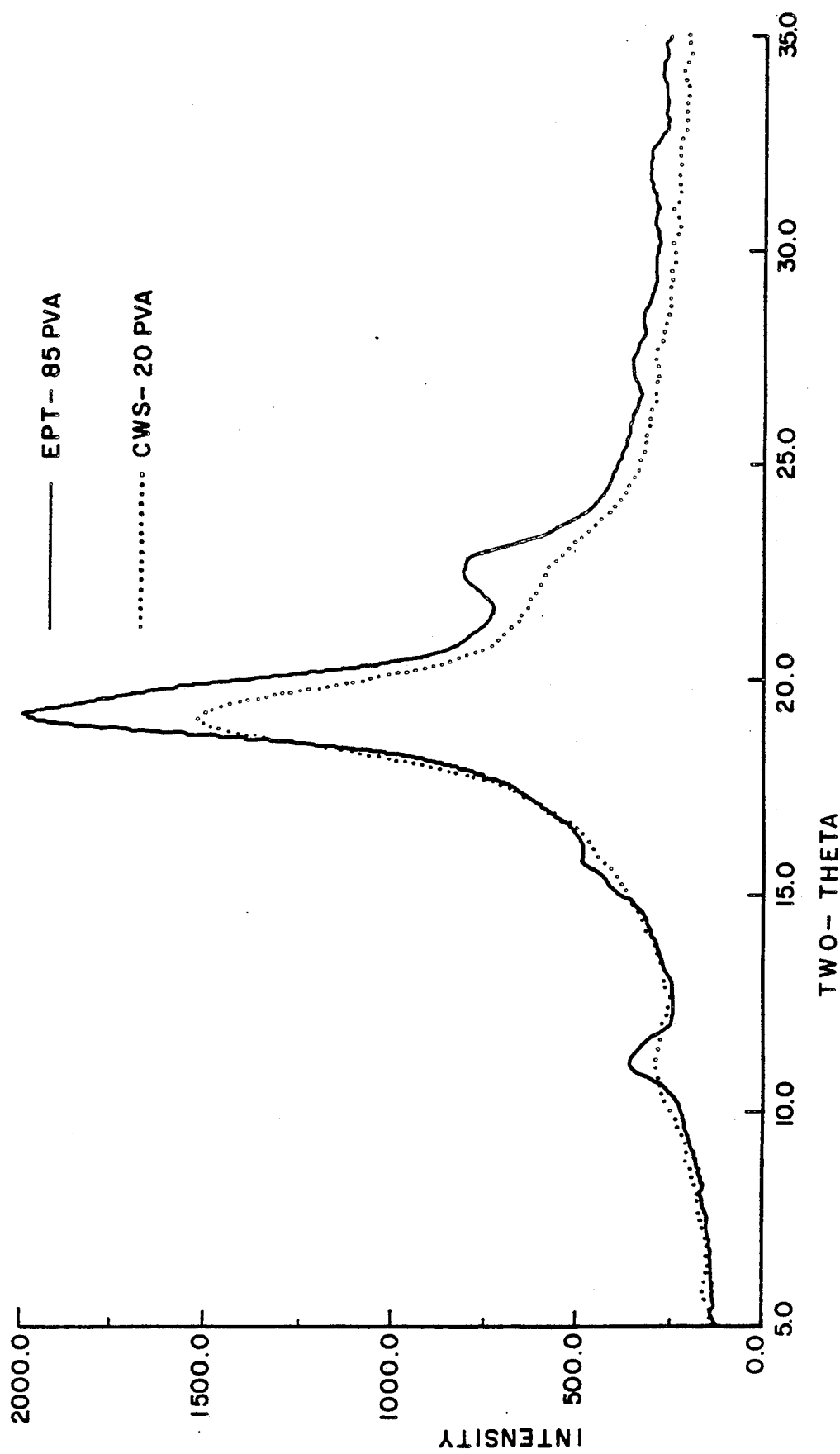
FIG. 1 is a wide angle x-ray diffraction scan of two copolymers of vinyl alcohol with methyl acrylate which can be used in this invention. Crystalline PVA/MA 9% copolymer is a crystalline vinyl alcohol copolymer containing 9 percent methyl acrylate. Amorphous PVA/MA 6% copolymer is a substantially amorphous vinyl alcohol copolymer with 6% methyl acrylate.

As a general comment on the nomenclature used in connection with the rate of release of active ingredient from the tablets of the present invention, there is lack of uniformity between medical applications on the one hand and agricultural and/or industrial applications on the other hand. Accordingly, the rate of release has been arbitrarily classified for the purpose of the present disclosure and claims into the following rough categories: instant (a few seconds to a few minutes), immediate (30 minutes), short (90% released in 4 hours), intermediate (85-90% released in 1-2 days), and extended sustained (90% released in 4 days).

Binders

Commercially available polyvinyl alcohols which have the physical and chemical characteristics required for this invention are the Elvanol ® polyvinyl alcohol homopolymers, which are manufactured and sold by E. I. du Pont de Nemours and Company. These crystalline polymers have viscosities of 10-70 mPa.sec; number average molecular weight $\overline{M}n$ of 25,000-100,000; polydispersity of 1.4 to 2.6; surface area of 0.6-6.0; percent hydrolysis of 99.0-99.8; and a particle size distribution such that less than 5% is retained on a 20 mesh (0.833 mm) screen, less than 50% is retained on an 80 mesh (0.175 mm) screen, more than 70% is retained on a 200 mesh (0.074 mm) screen, and more than 90% is retained on a 400 mesh (0.038 mm) screen. In a photomicrograph, the polymers have the appearance of spheroidal clusters of spheroidal particles. The particles are capable of flowing spontaneously through an orifice of 10 mm diameter and are compressible as pure material to a tablet having a hardness greater than 30SCU with a compression pressure of $12.3 \times 10^6$ kg/m$^2$.

A preferred Elvanol ® PVA is Elvanol ® HV, which is referred to below as crystalline PVA-homopolymer. This polymer has a viscosity of 55-65 mPa.sec.

Crystalline vinyl alcohol/methyl acrylate copolymers for use in this invention can be prepared in a continuous polymerizer at 70-103 kPa from vinyl acetate monomer (VA) and methyl acrylate (MA) mixtures. The VA/MA mixture is purged with nitrogen to remove any residual air, and is mixed with methanol, recycled solvents and Vazo ® 64 2,2'-azobis-(isobutyronitrile), the initiator for the reaction. This mixture is continuously fed to a stirred polymerizer kettle maintained under reflux. A solution containing vinyl acetate/methyl acrylate copolymer, methanol, methyl acetate and VA/MA is removed continuously and polymerization is inhibited by addition of hydrazine monoacetate. Then, the solution is fed to the top of a stripper column. Methanol vapors at atmospheric pressure enter the bottom of the column and strip the VA/MA from the polymer. The VA/MA and methanol vapors are removed from the top of the column and a solution containing vinyl acetate/methyl acrylate copolymer, methanol and methyl acetate is removed from the bottom.

The copolymer/methanol/methyl acetate solution is pulse-fed to a stirred alcoholysis kettle maintained at a constant temperature of 60-65° C. As the vinyl acetate copolymer is converted to vinyl alcohol copolymer, methyl acetate is produced. The vinyl alcohol copolymer is insoluble in the methanol/methyl acetate and the polymer precipitates. The slurry overflows to a holding tank and is neutralized to pH 5-7 by addition of acetic acid.

The neutralized slurry is then heated to a temperature of 110°-140° C. and held for 5-20 minutes at this temperature. This heat treatment improves the cold water slurrying characteristics of the copolymer, and causes crystallization in at least the surface portion of the PVA particles. The slurry is centrifuged and the cake is dried in a steam tube rotary dryer. Solvents and monomer are recovered and recycled.

The solution/slurry alcoholysis step described above is key to obtaining granular PVA having greater than 98% hydrolysis and the other physical characteristics required for use in this invention. In other commercial PVA manufacturing processes the polyvinyl acetate (PVAc) solution is run out onto a belt and the belt is run through an alkaline methanol solution to convert the polymer to PVA. This alcoholysis method results in relatively low percent hydrolysis and produces non-spheroidal PVA particles with poor flow and compression characteristics.

The use of pulse feed alcoholysis to produce granular PVA is disclosed in Tanner U.S. Pat. No. 3,296,236, issued Jan. 3, 1967. Heat treatment to improve water slurrying properties is disclosed in Bristol U.S. Pat. No. 3,654,247, issued Apr. 4, 1972, and Bristol U.S. Pat. No. 3,497,487, issued Feb. 24, 1970. Stripping VA monomer is disclosed in Lankton et al. U.S. Pat. No. 3,259,555, issued July 5, 1966. Use of hydrazine to inhibit vinyl polymerization is disclosed in Bristol et al. U.S. Pat. No. 3,583,963, issued June 8, 1971. The complete disclosures of these patents are incorporated herein by reference.

A PVA copolymer containing 9% methyl acrylate has been prepared by the above-described procedure. This product is referred to herein as crystalline PVA/MA 9% copolymer. Crystalline vinyl alcohol/-methyl methacrylate copolymers for use in this invention can be made by the same procedure, substituting methyl methacrylate for methyl acrylate. The methyl acrylate and methyl methacrylate are present in the vinyl alcohol copolymers as lactones. For the PVA copolymers, the percentage refers to the grams of co-monomer (MA or MMA) per 100 grams of polymer, assuming the original molecular weight of the comonomer.

Substantially amorphous PVA homopolymer and copolymers with methyl acrylate and methyl methacrylate can be prepared by the above-described procedure, except eliminating the heat treatment step. However, for making the amorphous polymers used in the examples a modified procedure was used. The modified polymerization procedure uses sodium nitrite instead of hydrazine monoacetate to stop the polymerization and uses citric acid to inhibit ester exchange reactions. Stripping of the polymerizer kettle bottoms is accomplished in a vacuum oven overnight at 75° C. to remove the VA monomer, methanol and methyl acetate. The polymerizer kettle is operated continuously at 83 kPa. As the PVAc solution is removed from the kettle, polymerization is inhibited by addition of sodium nitrite, then the polymer solution is stripped as described above.

The modified alcoholysis procedure is batch, rather than semi-continuous (pulse-fed) as in the previously-described procedure. The alcoholysis begins by dissolving the polymer obtained as just described in methanol. A solution containing 50 g of polymer, 300 ml of methanol, and 75 ml of methyl acetate is poured into a high-speed, explosion-proof blender. Seventy-five ml of 10% (in methanol) sodium methylate is slowly added to the mixture as it is blended. Temperature is not controlled in the alcoholysis kettle; the unit starts out at ambient temperature and temperature rises due to reaction and mixing. After a gel phase has formed and been broken, the mixture is blended for 10 more minutes. The mixture is then neutralized to pH 5-7 with acetic acid. The cake is then filtered, washed with methanol, filtered again, screened through a 20 mesh (0.833 mm) screen, and dried in a vacuum oven at 70° C. The polymer is not heat-treated.

PVA homopolymer made by this modified procedure is referred to herein as amorphous PVA homopolymer. A PVA copolymer containing 6% methyl acrylate made by this modified procedure is referred to herein as amorphous PVA/MA 6% copolymer. The methyl acrylate is present in the final product as a lactone.

FIG. 1 is a wide angle x-ray diffraction scan for crystalline PVA/MA 9% copolymer and amorphous PVA/MA 6% copolymer. A polymer is considered amorphous if an X-ray diffraction scan of the polymer is characterized by the lack of distinct peaks in the angular region of the scan dominated by chain-chain interactions. These crystalline peaks are the equatorial reflections (Miller indices hko for a polymer where the polymer-chain axis is coincident with the c-axis of the unit cell). More specifically, the lack of distinct peaks in the region between 13 degrees and 35 degrees 2-theta can be tested by the lack of any distinct minima in this region other than the low- and high-angle limits of the broad amorphous peak. A distinct minimum is characterized by having a slope of the first derivative of zero where the curvature or the second derivative is positive or concave upwards. A scan for this test can be obtained on any well-aligned reflection powder diffractometer employing a nickel filter or monochromating crystal and pulse-height analysis set to pass symmetrically 90% of the characteristic copper radiation.

Referring to FIG. 1, it will be observed that amorphous PVA/MA 6% copolymer produced no distinct peak in the angular region dominated by chain-chain interactions, i.e., the region of 15-35 degrees 2-theta, other than the region 19 degrees 2-theta which corresponds to the amorphous peak. A shoulder in the 23-degree 2-theta region suggests some chain-chain interaction, but the polymer is considered to be substantially amorphous. Crystalline PVA/MA 9% copolymer, on the other hand produced, a distinct peak at 23 degrees 2-theta, indicating that it is at least partially crystalline. It is believed that the particles of crystalline PVA/MA 9% copolymer have a crystalline surface and amorphous core.

X-ray diffraction scans for crystalline PVA homopolymer and amorphous PVA homopolymer are similar to those for the crystalline and amorphous copolymers, respectively.

A crystalline granular polymer can be converted to a substantially amorphous granular polymer by dissolving in a methanol/acetone mixture and reprecipitating by addition of methanol without heat treatment. Similarly, a substantially amorphous polymer can be converted to a crystalline polymer by slurrying in methanol and heat treating under conditions similar to the heat treatment described above.

It is possible, though not preferred, to use conventional binders, such as those mentioned in the Background of the Invention section, in combination with the vinyl alcohol polymers described above. For example, the vinyl alcohol polymer could constitute 30-100% of total binder and 0-70% could be one or more of the conventional binders or a non-granular vinyl alcohol polymer.

Tableting

For preparation of tablets binder and active ingredient substance are mixed in conventional manner, using conventional equipment. The mixture can be wet granulated in the conventional way, but dry granulation is preferred and direct compression is most preferred.

The active ingredient can be any active ingredient or mixture of active ingredients capable of being administered or employed in tablet form. We have formulated oxycodone, nalbuphine, phenylpropanolamine, and theophylline as PVA tablets. Examples of other active ingredients which can be used are those drugs and drug classes listed in Schor et al. U.S. Pat. No. 4,389,393, issued June 21, 1983, the disclosure of which is incorporated herein by reference.

The ratio of active ingredient to binder will generally be in the range of 3:1 to 1:10, preferably 2:1 to 1:5, most preferably 1:1 to 1:3.

In addition to binder and active ingredient, other commonly used tablet fillers and excipients can be used in conventional amounts. Inclusion of magnesium stearate as a lubricant in an amount of up to about 1% of the total ingredients is preferred. Other excipients which can be used include other lubricants, flavoring agents, disintegrants, and coloring agents.

Any conventional tableting machine can be used, and tablets can be made in any conventional size and shape, e.g., discoid, oblong, or triangular. Compression pressures up to the maximum provided by the machine can be used, e.g., $1.6 \times 10^8$ kg/m$^2$ or more, but a pressure in the range of about $2-5 \times 10^6$ kg/m$^2$ will usually be sufficient and preferred for economy.

EXAMPLES

In Examples 1-4, below, the drug release characteristics were measured in vitro. Dissolution was performed using a procedure described in the U.S. Pharmacopeia XXI, page 1243 (1985). This procedure involves use of a 1 liter glass vessel immersed in water at 30° C. or 37° C. and an appropriate dissolution medium (0.1 N HCl, pH 7.4 phosphate buffer, buffered saline or water). This vessel is stirred at a constant rate (25, 50 or 100 RPM) for the duration of the dissolution procedure to determine the amount of drug released. In Examples 1 to 4, 900 ml of distilled water was used set at 37° C. with a stirring speed of 50 RPM.

Figure 3:
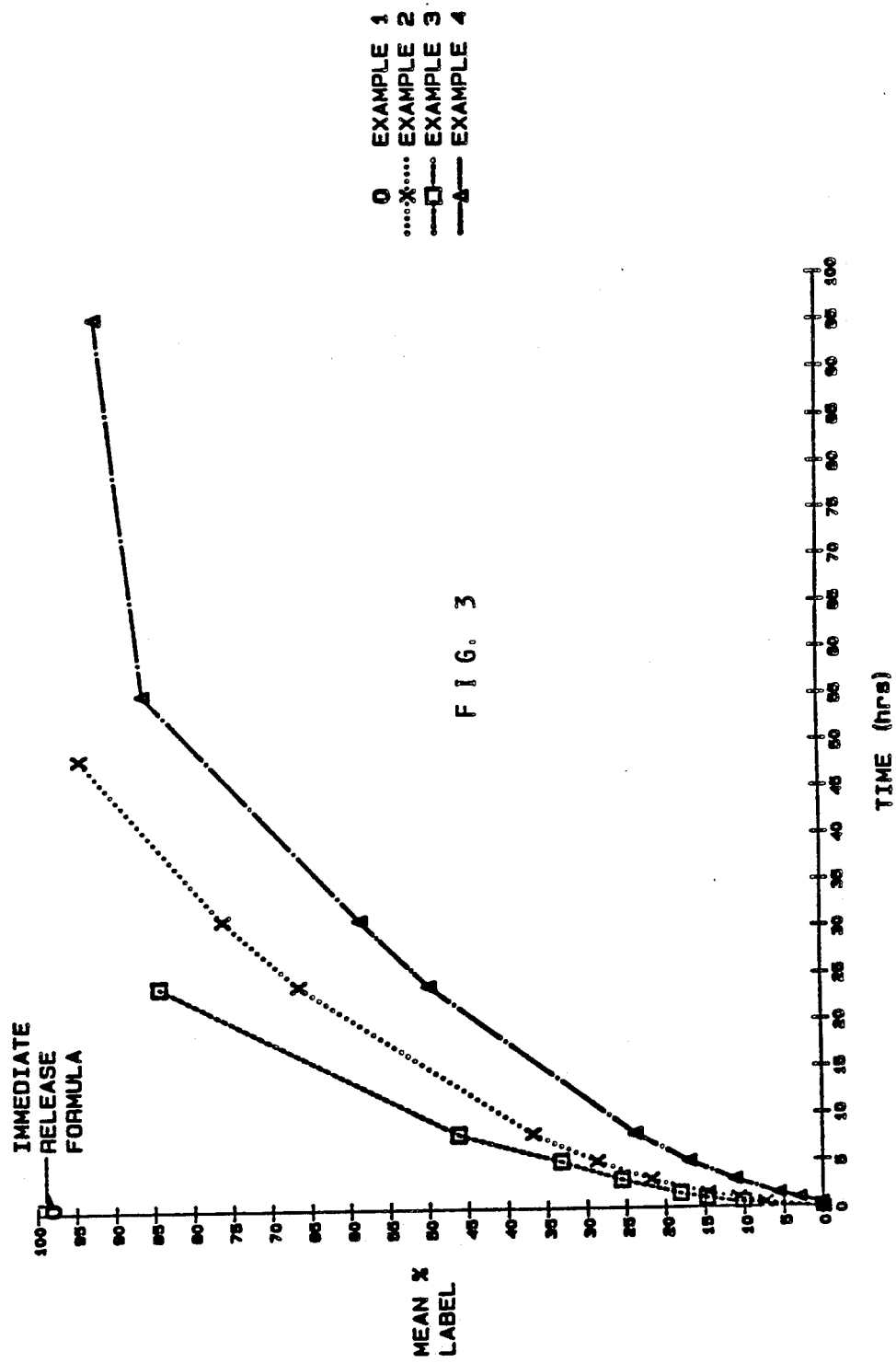
FIG. 3 is a plot showing dissolution profile of theophylline from PVA tablets prepared as described in Examples 1–4.

The dissolution profile for Examples 1 to 4 are shown in FIG. 3.

Figure 4:
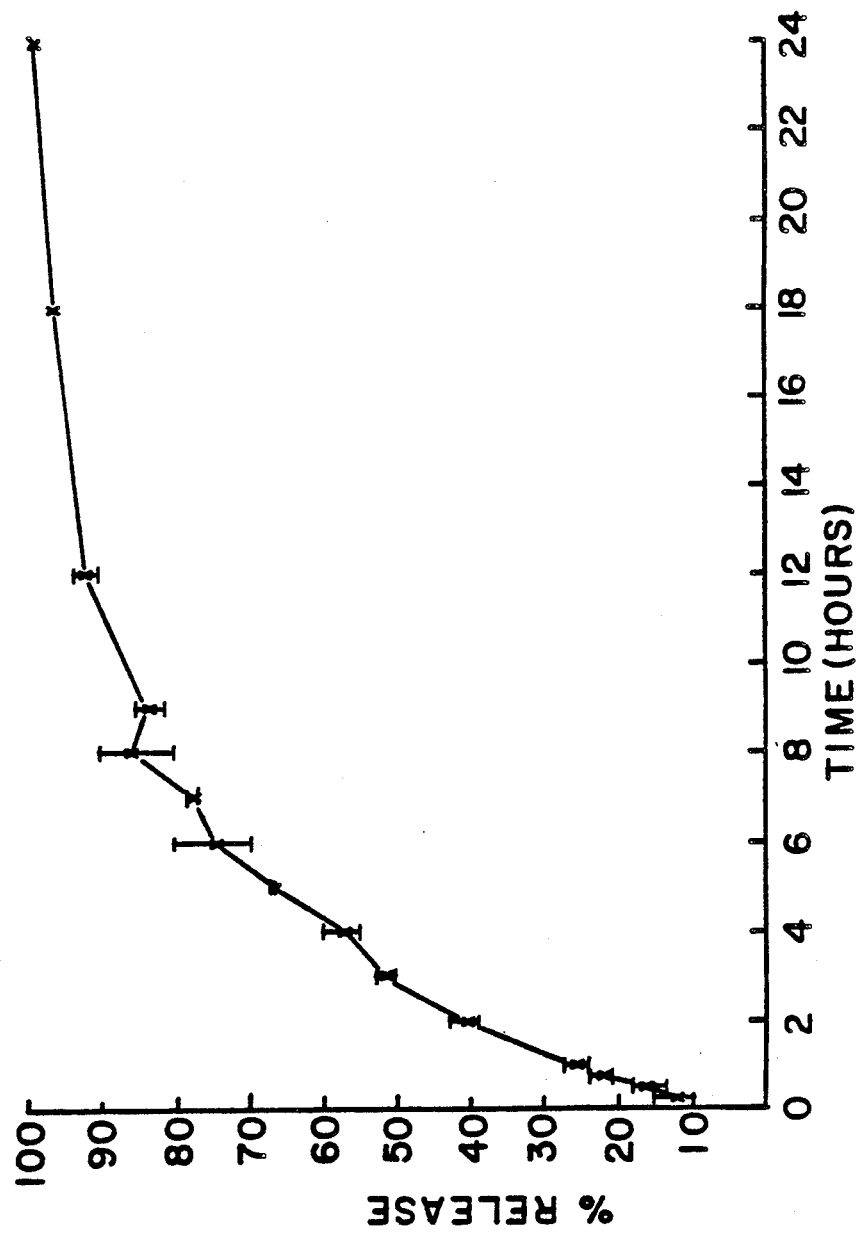
FIG. 4 is a plot showing dissolution profile of phenylpropanolamine (PPA) from PVA tablets prepared as described in Example 5.

In Example 5, drug release was measured in vitro by the same procedure, where the dissolution medium contained 1000 ml of 0.1 N HCl and was stirred at 50 RPM. The dissolution profile is shown in FIG. 4.

EXAMPLE 1

Immediate Release (100% Release in 30 Minutes)

Theophylline Formula

| Ingredient | mg/Tablet |
| --- | --- |
| Theophylline | 200 |
| Crystalline PVA homopolymer | 200 |
| Magnesium Stearate | 5 |

| Ingredient | mg/Tablet |
|---|---|
| | 405 |

Compounding
1. Blend via geometric dilution.
2. Compress on Manesty F-3 single punch tablet press at 2.7×10⁶ kg/m² pressure with ⅜ inch (9.53 mm) diameter standard concave tooling to form tablets with average hardness of 12SCU.

EXAMPLE 2

Intermediate Release Formula (90% Release in 48 Hours)

Same formula and procedure as Example 1 except substitution of non-heat treated amorphous PVA homopolymer. Average hardness of resulting tablets 12 SCU.

EXAMPLE 3

Intermediate Release Formula (85% Release in 24 Hours)

| Ingredient | mg/Tablet |
|---|---|
| Theophylline | 200 |
| Crystalline PVA homopolymer | 100 |
| Amorphous PVA/MA 6% copolymer | 100 |
| Magnesium Stearate | 5 |
| | 405 |

Compounding
1. Blend via geometric dilution
2. Slug to improve blend flowability—grind to acceptable tablet granulation.
3. Compress on Manesty F-3 tablet press at 2.7×10⁶ Kg/m² pressure with 9.53 mm diameter standard concave tooling to make tablets with a hardness of 12SCU.

EXAMPLE 4

Extended Sustained Release (90% Release in 96 Hours)

| Ingredient | mg/Tablet |
|---|---|
| Theophylline | 200 |
| Amorphous PVA/MA 6% copolymer | 200 |
| Magnesium Stearate | 5 |
| | 405 |

Same method of compounding as Example 3. Average hardness of resulting tablets 12 SCU.

EXAMPLE 5

Phenylpropanolamine (PPA) Sustained Release Tablet (In Vitro—100% Release in 24 Hours)

| Ingredient | mg/Tablet |
|---|---|
| Amorphous PVA/MA 6% copolymer | 237 |
| Phenylpropanolamine (PPA) | 60 |
| Magnesium Stearate | 3 |
| | 300 |

Compounding

1. Blend via geometric dilution.
2. Tablet on Manesty F-3 single punch tableting machine with ⅜ inch (9.53 cm) diameter standard concave tooling compression pressure of 4.8×10⁶ kg/m² to form compacts at the target weight of 300 mg, tablet hardness=12 SCU.

Three dogs were administered, in a cross-over fashion, phenylpropanolamine.HCl i.v. (3 mg/kg), orally (30 mg in a gelatin capsule) and in the above PVA/MA copolymer tablet composition containing 60 mg of phenylpropanolamine.HCl. Plasma samples were collected as a function of time and frozen until analysis of drug concentration.

Analysis of phenylpropanolamine in plasma was performed by high pressure liquid chromatography (HPLC). Phenylethylamine, as internal standard, and 3.5% aqueous sodium carbonate were added to 0.5 ml plasma samples. Two extractions into ethyl acetate and back extraction into 0.2 ml of 5% aqueous acetic acid were performed. The acetic acid solution was injected onto the HPLC. The mobile phase consisted of a mixture of 11% (v/v) acetonitrile and 0.2% (v/v) 1N.HCl in 0.004M aqueous sodium heptane sulfonate. A 25 cm CN column and U.V. detection at=210 nm were employed. Phenylpropanolamine/phenylethylamine peak area ratios were used in construction of calibration curves.

Figure 2:
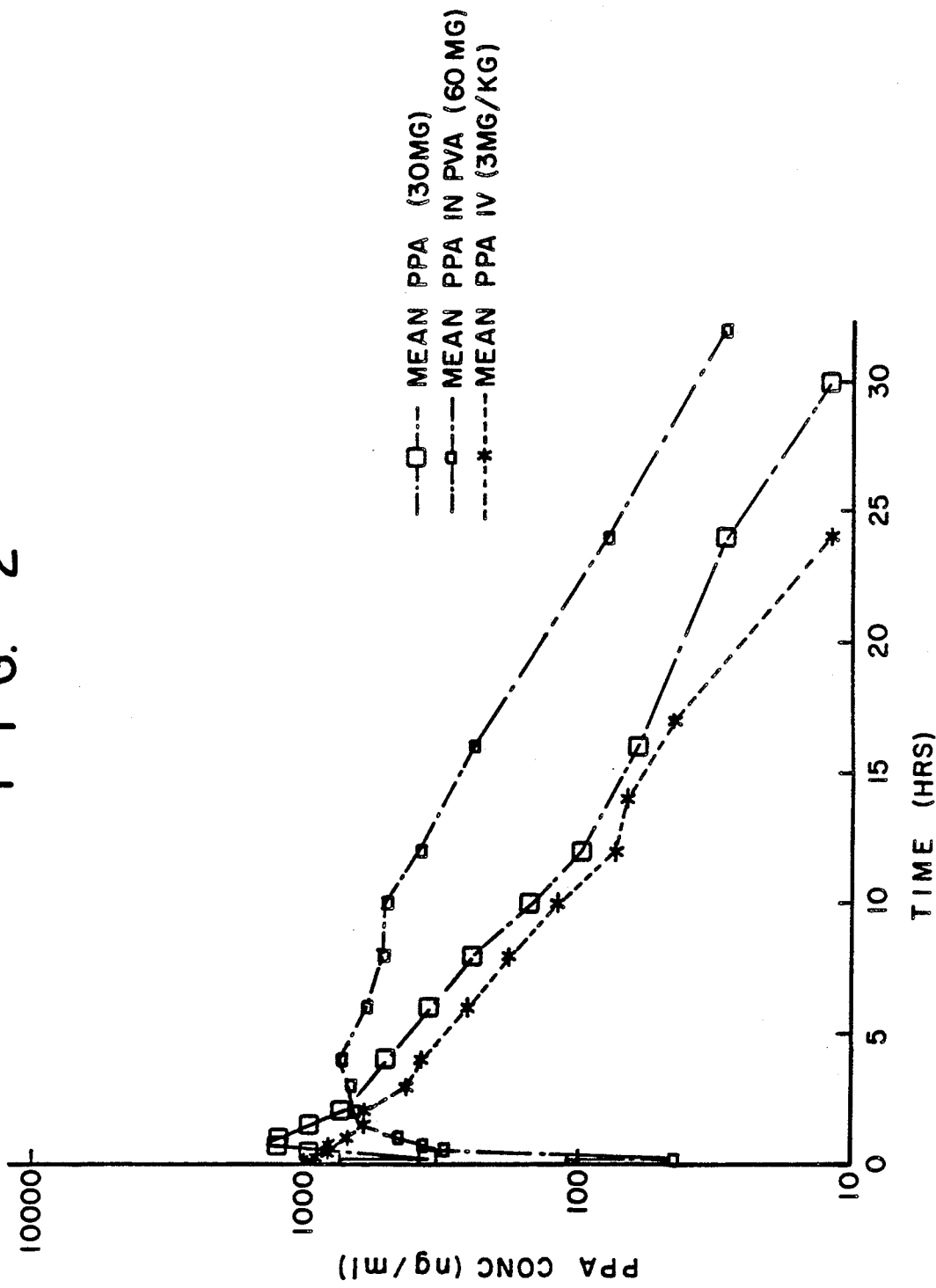
FIG. 2 is a plot of phenylpropanolamine (PPA) concentration in plasma of dogs administered the drug (PPA) intravenously, orally by capsule and orally in an amorphous PVA/MA 6% copolymer tablet of this invention, and shows the prolonged release of drug by the tablet.

The area under each plasma phenylpropanolamine concentration vs. time curve (AUC) (FIG. 2) was calculated using the trapezoidal method. Bioavailability (F) was estimated by:

$$F = \frac{AUC(po) \times Dose\ (iv)}{SUC(iv) \times Dose\ (po)} \times 100$$

F represents the percentage of the administered dose absorbed into plasma.

Sustained plasma concentrations of the drug were observed for 12 hours (FIG. 2), i.e., a relatively constant plasma concentration is achieved.

The oral bioavailability of phenylpropanolamine.HCl when administered in the amorphous PVA/MA 6% copolymer formulation was 78+4% (mean+SD in 3 dogs) and that of phenylpropanolamine.HCl when administered in a gelatin capsule was 98+8%.

EXAMPLE 6

Tablets containing 50% of potassium monopersulfate (commercial oxidizing agent available from the Du Pont Company under the trademark Oxone®) and 50% of an amorphous PVA/MA 9% copolymer were prepared according to the technique described in Example 1. The rate of release of the active ingredient is shown in FIG. 5, which is a plot of percent release versus time in hours. It can be seen that 90% of the active ingredient was released in 4 hours, where a plateau was reached. These can be characterized as short release tablets.

When comparing these results with those of Example 4, wherein a fairly similar PVA/MA copolymer was used in the same proportion as the tableting material, one notes a considerable difference in the respective rates of release. This may be due to the difference in the properties of the respective active ingredients. While both theophylline and potassium persulfate have similar water solubilities, the persulfate is an energetic oxidizing agent and tends to release gas on contact with water and with organic copolymer.

EXAMPLE 7

A commercial herbicide material (metasulfuron methyl, available from the Du Pont Company) was compounded according to the technique of Example 1 as follows:

metasulfuron methyl—70 parts
Crystalline PVA/MA 9% copolymer—30 parts

When added to a low electrolyte strength nitrogen fertilizer (28% N, 0% K, 0% P), the active ingredient was completely released in 3 minutes; when added to high electrolyte strength nitrogen fertilizer (32% N, 0% K, 0% P), it was completely released in 7 minutes. These were instant release tablets, suitable for use in fertilizer spray solutions.

EXAMPLE 8

Hexazinone herbicide was compounded according to the technique of Example 1 as follows:

Hexazinone—20 parts
Crystalline EVA hompolymer—80 parts

The rate of release of the active ingredient in water was 30 seconds; thus the release was instant. These tablets are suitable for use in aerial broadcasting, where it is not necessary to dust the plants but it is sufficient to deliver the systemic herbicide to the roots, as it dissolves in the moisture of the soil.

EXAMPLE 9

A slug bait could be compounded as follows:

wheat middlings (and poison)—60 parts
Amorphous PVA/MA 9% copolymer—40 parts

In a test in which no poison was used, disintegration of tablets in water occurred in 30 min. The pellets were palatable to slugs. By contrast, standard prior art molluscicide tablets are formulated with sugar. Under the same accelerated laboratory conditions, such sugar-formulated tablets disintegrate in 20 minutes. Under field conditions, tablets of the present invention are only slowly rained away, while the prior art tablets are rained away considerably faster. It is estimated that the tablets of the present invention (when formulated with active ingredient, such as, for example metaldehyde) will have sufficiently long sustained activity to last for a full season, while the prior art tablets normally must be applied twice during the same period.

All the above examples show the advantages of using the polymers of the present invention as tableting materials. However, the actual rates of release of the active ingredient present in such tablets will depend to some extent not only on the polymer itself but also on the nature of the active ingredient, including its water solubility and activity or chemical reactivity.

We claim:

1. A method of making a compressed tablet for delivery of an active ingredient comprising mixing the active ingredient and binder in powder form and compressing the mixture into a tablet, characterized by that the binder consists essentially of at least one polymer selected from the group consisting of amorphous polyvinyl alcohol, copolymers of vinyl alcohol with up to about 10 mole percent methyl acrylate or methyl methacrylate, and blends of such copolymers with polyvinyl alcohol, the polymer having: a number average molecular weight in the range of about 25,000 to 100,000; polydispersity in the range of about 1.4 to 2.6; viscosity in 4% aqueous solution in the range of about 10 to 70 mPa.sec; a surface area in the range of about 0.6 to 6.0 $m^2/g$; percent hydrolysis of at least 98%; the polymer being in the form of spheroidal particles arranged in spheroidal clusters, with a size distribution such that less than about 5% of the polymer is retained on a 20 mesh (0.833 mm) screen, less than about 50% of the polymer is retained on an 80 mesh (0.175 mm) screen, and more than about 70% is retained on a 200 mesh (0.074 mm) screen.

2. Method of claim 1 wherein the polymer is capable of flowing spontaneously through an orifice of 10 millimeter diameter and is compressible to a tablet having a hardness greater than about 30 Strong-Cobb units with a compression pressure of $12.3 \times 10^6$ $kg/m^2$.

3. Method of claim 2 wherein the binder consists essentially of at least one polymer selected from the group consisting of polyvinyl alcohol and copolymers of vinyl alcohol with up to about 10 percent methyl acrylate.

4. Method of claim 3 wherein the binder consists essentially of substantially amorphous polymer, whereby the resulting tablet provides prolonged active ingredient release.

5. Method of claim 3 wherein the binder consists essentially of at least partially crystalline copolymer of vinyl alcohol with up to about 10 percent methyl acrylate or a blend of such copolymer with at least partially crystalline polyvinyl alcohol, whereby the resulting tablet provides substantially immediate active ingredient release.

6. Method of claim 3 wherein the binder consists essentially of a mixture of substantially amorphous polymer and at least partially crystalline polymer, wherein each of the above polymers is selected from the group consisting of polyvinyl alcohol and copolymers of vinyl alcohol with up to about 10 percent methyl acrylate or methyl methacrylate, whereby the resulting tablet provides intermediate active ingredient release.

7. Method of claim 3 wherein the mixture is dry granulated prior to compression to tablet form.

8. Method of claim 3 wherein the tablet is formed by direct compression of the mixture without prior granulation.

9. Compressed tablet for active ingredient delivery consisting essentially of active ingredient and binder consisting essentially of about 30–100% of polymer selected from the group consisting of amorphous polyvinyl alcohol, copolymers of vinyl alcohol with about 1 to 10 mole percent methyl acrylate or methyl methacrylate, and blends of such copolymers with polyvinyl alcohol, each polymer having: a number average molecular weight in the range of about 25,000 to 100,000; polydispersity in the range of about 1.4 to 2.6; viscosity in 4% aqueous solution in the range of about 10 to 70 mPa.sec; a surface area in the range of about 0.6 to 6.0 $m^2/g$; percent hydrolysis of at least 98%; the polymer being in the form of spheroidal particles arranged in spheroidal clusters, with a size distribution such that less than about 5% of the polymer is retained on a 20 mesh (0.833 mm) screen, less than about 50% of the polymer is retained on an 80 mesh (0.175 mm) screen, and more than about 70% is retained on a 200 mesh (0.074 mm) screen; and 0 to about 70% of at least one member of the group consisting of polyvinyl alcohol, hydroxypropylmethylcellulose, microcrystalline cellulose, lactose, acacia mucilage, tragacanth mucilage, starch mucilage, alginates, sugar, and polyvinylpyrrolidone.

10. Compressed tablet of claim 9 wherein the active ingredient is a drug to be administered orally.

11. Compressed tablet of claim 9 wherein the binder consists essentially of 30–100% of vinyl alcohol copolymer with 1 to 10 mole percent methyl-acrylate and 0–70 percent granular, crystalline polyvinyl alcohol.

12. Compressed tablet of claim 11 wherein the active ingredient is a drug to be administered orally.

13. Compressed tablet of claim 11 wherein the active ingredient is an agricultural chemical.

14. Compressed tablet of claim 11 wherein the active ingredient is a veterinary chemical.

15. Compressed tablet of claim 11 wherein the active ingredient is a personal care chemical.

16. Compressed tablet of claim 11 wherein the vinyl alcohol copolymer is substantially amorphous, whereby the tablet provides prolonged active ingredient release.

17. Compressed tablet of claim 16 wherein the binder consists essentially of substantially amorphous copolymer.

18. Compressed tablet for immediate oral drug delivery consisting essentially of drug substance and binder consisting essentially of at least one polymer selected from the group consisting of copolymers of vinyl alcohol with up to 10 mole percent of methyl acrylate or methyl methacrylate and blends of such copolymers with polyvinyl alcohol, each polymer having: a number average molecular weight in the range of about 25,000 to 100,000; polydispersity in the range of about 1.4 to 2.6; viscosity in 4% aqueous solution in the range of about 10 to 70 mPa.sec; a surface area in the range of about 0.6 to 6.0 $m^2$/g; percent hydrolysis of at least 98% the polymer being in the form of spheroidal particles arranged in spheroidal clusters, with a size distribution such that less than about 5% of the polymer is retained on a 20 mesh (0.833 mm) screen, less than about 50% of the polymer is retained on an 80 mesh (0.175 mm) screen, and more than about 70% is retained on a 200 mesh (0.074 mm) screen, characterized by that the polymer is at least partially crystalline, whereby the tablet disintegrates quickly when place in dilute acid.

19. Compressed tablet of claim 18 wherein the polymer is polyvinyl alcohol.

20. Compressed tablet of claim 18 wherein the polymer is a copolymer of vinyl alcohol and methyl acrylate.

21. Compressed tablet of claim 18 wherein the active compound is set granulated with an aqueous solution ranging in concentration from 1 to 10% polyvinyl alcohol homopolymer and/or copolymer.

* * * * *

UNITED STATES PATENT AND TRADEMARK OFFICE
CERTIFICATE OF CORRECTION

PATENT NO. :    4,990,335
DATED      :    February 5, 1991
INVENTOR(S):    Linda R. Bateman, et al.

It is certified that error appears in the above—identified patent and that said Letters Patent is hereby corrected as shown below:

On the title page:
[75] Inventors: "David P. Beach-Coffin" should be
     -- David P. Coffin-Beach --.

Column 14, Claim 21, line 23, "set" should be -- wet --.

Signed and Sealed this

Thirtieth Day of June, 1992

Attest:

DOUGLAS B. COMER

*Attesting Officer*     *Acting Commissioner of Patents and Trademarks*